United States Patent [19]
Mathiowitz et al.

[11] Patent Number: 6,143,211
[45] Date of Patent: Nov. 7, 2000

[54] PROCESS FOR PREPARING MICROPARTICLES THROUGH PHASE INVERSION PHENOMENA

[75] Inventors: Edith Mathiowitz, Brookline, Mass.; Donald Chickering, III, Pfulgerville, Tex.; Yong S. Jong, Warwick, R.I.; Jules S. Jacob, Taunton, Mass.

[73] Assignee: Brown University Foundation, Providence, R.I.

[21] Appl. No.: 08/686,928

[22] Filed: Jul. 3, 1996

Related U.S. Application Data

[60] Provisional application No. 60/001,365, Jul. 21, 1995.

[51] Int. Cl.[7] .............................. B01J 13/04; B01J 13/06
[52] U.S. Cl. ......................... 264/4; 264/4.1; 427/213.36
[58] Field of Search .......................... 427/213.36; 264/4, 264/4.1

[56] References Cited

U.S. PATENT DOCUMENTS

| | | | |
|---|---|---|---|
| 3,369,306 | 2/1968 | Sternberg et al. . | |
| 3,615,024 | 10/1971 | Michaels . | |
| 3,943,063 | 3/1976 | Morishita et al. . | |
| 4,187,194 | 2/1980 | Wellman et al. | 252/316 |
| 4,542,042 | 9/1985 | Samejima et al. | 427/213.36 |
| 4,624,776 | 11/1986 | Long et al. | 208/302 |
| 4,637,905 | 1/1987 | Gardner . | |
| 4,731,486 | 3/1988 | Abatjoglou et al. | 568/454 |
| 4,861,627 | 8/1989 | Mathiowitz et al. . | |
| 4,997,454 | 3/1991 | Violante et al. | 210/639 |
| 5,049,322 | 9/1991 | Devissaguet et al. . | |
| 5,075,109 | 12/1991 | Tice et al. . | |
| 5,118,528 | 6/1992 | Fessi et al. | 427/213.36 |
| 5,288,502 | 2/1994 | McGinity et al. . | |
| 5,384,133 | 1/1995 | Boyes . | |
| 5,407,609 | 4/1995 | Tice . | |
| 5,460,831 | 10/1995 | Kossovky et al. . | |
| 5,466,587 | 11/1995 | Fitzpatrick-McElligott et al. . | |
| 5,474,780 | 12/1995 | Chang . | |
| 5,478,744 | 12/1995 | Sanford et al. . | |
| 5,478,745 | 12/1995 | Samulski et al. . | |
| 5,480,914 | 1/1996 | Meadows . | |
| 5,498,421 | 3/1996 | Grinstaff et al. . | |
| 5,516,670 | 5/1996 | Kuehnle et al. . | |
| 5,518,731 | 5/1996 | Meadows . | |
| 5,741,522 | 4/1998 | Violante et al. | 424/489 |
| 5,766,635 | 6/1998 | Spenleuhauser et al. | 424/489 |

FOREIGN PATENT DOCUMENTS

| | | |
|---|---|---|
| 248 531 | 12/1987 | European Pat. Off. . |
| WO 94/23699 | 10/1994 | WIPO . |
| WO 94/23738 | 10/1994 | WIPO . |
| WO 95/24929 | 12/1995 | WIPO . |
| WO 95/35097 | 12/1995 | WIPO . |

OTHER PUBLICATIONS

J.H. Eldridge et al., "Biodegradable poly (DL–lactide–co–hlycolide) microspheres" *Charachteristics and Use of New–Generation Adjuvants, 44th Forum in Immunology,* pp. 557–563.

Joseph M. Pilewski et al., "Adenovirus–mediated Gene Transfer to Human Bronchial Submucosal Glands Using Xenografts", *American Physioligical Society*, 1995, pp. L657–L665.

International Search Report for PCT/US96/12024.

Eldridge et al. "Biodegradable Microspheres as a Vaccine Delivery system" *Molecular Immunology*, 1991, vol. 28, No.3, pp.287–294.

Eldridge et al. "Pulsatile Delivery of vaccines" *Paperback APV*, 1993, vol.33, pp.163–176.

Fynan et al. "DNA vaccines:Protective immunizations by parenteral, mucosal, and gene–gun inoculations" Proc. Natl. Acad. Sci. USA Dec. 1993, vol. 90, pp. 11478–11482.

Staats et al. "Mucosal immunity to infection with implications for vaccine development" *Cur. Opin. in Immun.* 1994, vol. 6 pp.572–583.

Chickering et al. "Bioavailability of Bioadhesive Polyanhydride Delivery Systems" Proceed. Intrn.Symp. Control. Rel. Bioact.Mater. Jul./Aug. 1995 vol. 22, pp.169–170.

Orkin et al. "Report and Recommendations . . . Gene Therapy" *NIH.* 1995, pp. 1–40.

Marshall "Gene Therapy's Growing Pains" *Science.* vol. 269, 1995, pp.1050–1055.

Hodgson "Advances in vector systems for gene therapy" *Exp. Opin. Ther. Patents* (1995) 5(5)pp.459–468.

Gander et al., Int. J. Pharm. 129 (1,2), p. 51–56, 1996.

*Primary Examiner*—Jeffrey C. Mullis
*Attorney, Agent, or Firm*—Wolf, Greenfield & Sacks, P.C.

[57] ABSTRACT

A process for preparing nanoparticles and microparticles is provided. The process involves forming a mixture of a polymer and a solvent, wherein the solvent is present in a continuous phase and introducing the mixture into an effective amount of a nonsolvent to cause the spontaneous formation of microparticles.

31 Claims, No Drawings

PROCESS FOR PREPARING MICROPARTICLES THROUGH PHASE INVERSION PHENOMENA

This application claims priority under 35 USC § 119 to U.S. application Ser. No. 60/001,365 entitled "Process for Preparing Microspheres Through Phase Inversion Phenomena" filed Jul. 21, 1995 by Edith Mathiowitz, Donald E. Chickering III, Yong S. Jong and Jules S. Jacob.

BACKGROUND OF THE INVENTION

Microparticles, microcapsules and microspheres (hereinafter "microparticles") have important applications in the pharmaceutical, agricultural, textile and cosmetics industry as delivery vehicles. In these fields of application, a drug, protein, hormone, peptide, fertilizer, pesticide, herbicide, dye, fragrance or other agent is encapsulated in a polymer matrix and delivered to a site either instantaneously or in a controlled manner in response to some external impetus (i.e., pH, heat, water, radiation, pressure, concentration gradients, etc.). Microparticle size can be an important factor in determining the release rate of the encapsulated material.

Many microencapsulation techniques exist which can produce a variety of particle types and sizes under various conditions. Methods typically involve solidifying emulsified liquid polymer droplets by changing temperature, evaporating solvent, or adding chemical cross-linking agents. Physical and chemical properties of the encapsulant and the material to be encapsulated can sometimes dictate the suitable methods of encapsulation, making only certain methodologies useful in certain circumstances. Factors such as hydrophobicity, molecular weight, chemical stability, and thermal stability affect encapsulation. Significant losses are frequently associated with multiple processing steps. These parameters can be particularly important in respect of encapsulating bioactive agents because losses in the bioactivity of the material due to the processing steps or low yields can be extremely undesirable.

Common microencapsulation techniques include interfacial polycondensation, spray drying, hot melt microencapsulation, and phase separation techniques (solvent removal and solvent evaporation). Interfacial polycondensation can be used to microencapsulate a core material in the following manner. One monomer and the core material are dissolved in a solvent. A second monomer is dissolved in a second solvent (typically aqueous) which is immiscible with the first. An emulsion is formed by suspending the first solution through stirring in the second solution. Once the emulsion is stabilized, an initiator is added to the aqueous phase causing interfacial polymerization at the interface of each droplet of emulsion.

Spray drying is typically a process for preparing 1–10 micron sized microspheres in which the core material to be encapsulated is dispersed or dissolved in a polymer solution (typically aqueous), the solution or dispersion is pumped through a micronizing nozzle driven by a flow of compressed gas, and the resulting aerosol is suspended in a heated cyclone of air, allowing the solvent to evaporate from the microdroplets. The solidified particles pass into a second chamber and are trapped in a collection flask. This process can result in 50–80% loss through the exhaust vent when laboratory scale spray dryers are used.

Hot melt microencapsulation is a method in which a core material is added to molten polymer. This mixture is suspended as molten droplets in a nonsolvent for the polymer (often oil-based) which has been heated to $\approx 10°$ C. above the melting point of the polymer. The emulsion is maintained through vigorous stirring while the nonsolvent bath is quickly cooled below the glass transition of the polymer, causing the molten droplets to solidify and entrap the core material. Microspheres produced by this technique typically range in size from 50 microns to 2 mm in diameter. This process requires the use of polymers with fairly low melting temperatures (i.e., <150° C.), glass transition temperatures above room temperature, and core materials which are thermo-stable.

In solvent evaporation microencapsulation, the polymer is typically dissolved in a water immiscible organic solvent and the material to be encapsulated is added to the polymer solution as a suspension or solution in organic solvent. An emulsion is formed by adding this suspension or solution to a beaker of vigorously stirring water (often containing a surface active agent to stabilize the emulsion). The organic solvent is evaporated while continuing to stir. Evaporation results in precipitation of the polymer, forming solid microcapsules containing core material.

A solvent evaporation process exists which is specifically designed to entrap a liquid core material in PLA, PLA/PGA copolymer, or PLA/PCL copolymer microcapsules. The PLA or copolymer is dissolved in a miscible mixture of solvent and nonsolvent, at a nonsolvent concentration which is immediately below the concentration which would produce phase separation (i.e., cloud point). The liquid core material is added to the solution while agitating to form an emulsion and disperse the material as droplets. Solvent and nonsolvent are vaporized, with the solvent being vaporized at a faster rate, causing the PLA or copolymer to phase separate and migrate towards the surface of the core material droplets. This phase separated solution is then transferred into an agitated volume of nonsolvent, causing any remaining dissolved PLA or copolymer to precipitate and extracting any residual solvent from the formed membrane. The result is a microcapsule composed of PLA or copolymer shell with a core of liquid material.

In solvent removal microencapsulation, the polymer is typically dissolved in an oil miscible organic solvent and the material to be encapsulated is added to the polymer solution as a suspension or solution in organic solvent. An emulsion is formed by adding this suspension or solution to a beaker of vigorously stirring oil, in which the oil is a nonsolvent for the polymer and the polymer/solvent solution is immiscible in the oil. The organic solvent is removed by diffusion into the oil phase while continuing to stir. Solvent removal results in precipitation of the polymer, forming solid microcapsules containing core material.

Phase separation microencapsulation is typically performed by dispersing the material to be encapsulated in a polymer solution by stirring. While continuing to uniformly suspend the material through stirring, a nonsolvent for the polymer is slowly added to the solution to decrease the polymer's solubility. Depending on the solubility of the polymer in the solvent and nonsolvent, the polymer either precipitates or phase separates into a polymer rich and a polymer poor phase. Under proper conditions, the polymer in the polymer rich phase will migrate to the interface with the continuous phase, encapsulating the core material in a droplet with an outer polymer shell.

A recent patent to Tice (U.S. Pat. No. 5,407,609) involves a phase separation microencapsulation process which attempts to proceed more rapidly than the procedure described in the preceding paragraph. According to Tice, a polymer is dissolved in the solvent. An agent to be encapsulated then is dissolved or dispersed in that solvent. The mixture then is combined with an excess of nonsolvent and is emulsified and stabilized, whereby the polymer solvent no longer is the continuous phase. Aggressive emulsification conditions are applied in order to produce microdroplets of the polymer solvent. After emulsification, the stable emulsion is introduced into a large volume of nonsolvent to extract the polymer solvent and form microparticles. The size of the microparticles is determined by the size of the microdroplets of polymer solvent. This procedure has the drawback that small particles can be obtained only with aggressive emulsification procedures. It also suffers the drawback that multiple processing steps are required to form the microparticles.

Phase inversion is a term used to describe the physical phenomena by which a polymer dissolved in a continuous phase solvent system inverts into a solid macromolecular network in which the polymer is the continuous phase. This event can be induced through several means: removal of solvent (e.g., evaporation; also known as dry process), addition of another species, addition of a non-solvent or addition to a non-solvent (also known as wet process). In the wet process, the polymer solution can be poured or extruded into a non-solvent bath. The process proceeds in the following manner. The polymer solution undergoes a transition from a single phase homogeneous solution to an unstable two phase mixture:polymer rich and polymer poor fractions. Micellar droplets of nonsolvent in the polymer rich phase serve as nucleation sites and become coated with polymer. At a critical concentration of polymer, the droplets precipitate from solution and solidify. Given favorable surface energy, viscosity and polymer concentrations, the micelles coalesce and precipitate to form a continuous polymer network.

Phase inversion phenomenon have been applied to produce macro and microporous polymer membranes and hollow fibers used in gas separation, ultrafiltration, ion exchange, and reverse osmosis. Structural integrity and morphological properties of these membranes are functions of polymer molecular weight, polymer concentration, solution viscosity, temperature and solubility parameters (of polymer, solvent and non-solvent). For wet process phase inversion, polymer viscosities must be greater than approximately 10,000 centipoise to maintain membrane integrity; lower viscosity solutions may produce fragmented polymer particles as opposed to a continuous system. Furthermore, it is known that the quicker a solution is caused to precipitate, the finer is the dispersion of the precipitating phase.

A phase inversion process has been employed to produce polymer microcapsules. The microcapsules are prepared by dissolving a polymer in an organic solvent, forming droplets of the solution by forcing it through a spinneret or syringe needle, (the size of which droplets determines the size of the final microcapsule), and contacting the droplets with a nonsolvent for the polymer which is highly miscible with the polymer solvent, thereby causing rapid precipitation of the outer layer of the droplet. The microcapsules must be left in contact with the nonsolvent until substantially all of the solvent has been replaced with nonsolvent. This process requires formation of a droplet with dimensions established prior to contacting the nonsolvent.

Each of the methods described before require the formation of an emulsion or droplets prior to precipitation of the final microparticle. The present invention provides a novel method of producing microparticles without the requirement of forming an emulsion prior to precipitation. Under proper conditions, polymer solutions can be forced to phase invert into fragmented spherical polymer particles when added to appropriate nonsolvents. We have utilized this spontaneous microparticle formation phase inversion process as a rapid, one step microencapsulation technique. The process is simple to perform, is suitable with a number of polymeric systems (including many common degradable and non-degradable polymers typically employed as controlled release systems), produces extremely small microparticles (10 nm to 10 $\mu$m) and results in very high yields.

SUMMARY OF THE INVENTION

It has been discovered that "phase inversion" of polymer solutions under certain conditions can bring about the spontaneous formation of discreet microparticles, including nanospheres. By using relatively low viscosities and/or relatively low polymer concentrations, by using solvent and nonsolvent pairs that are miscible and by using greater than ten fold excess of nonsolvent, a continuous phase of nonsolvent with dissolved polymer can be rapidly introduced into the nonsolvent, thereby causing a phase inversion and the spontaneous formation of discreet microparticles.

The process eliminates a step characteristic of the prior art, that is, creating microdroplets, such as by forming an emulsion, of the solvent. It likewise eliminates drawbacks associated with the microdroplet formation step of the prior art. The microdroplet formation step consumes time, can be disruptive of the agent to be encapsulated, and can be the limiting factor in determining the ultimate size of the formed microparticle. The process of the invention is simpler and quicker than those prior art methods because this step is eliminated. The invention has the advantage that it can be performed very rapidly, the entire process taking less than five minutes in some cases. The actual phase inversion and encapsulation can take place in less than 30 seconds. It also has the advantage of avoiding the agitation and/or shear forces to which the material to be encapsulated otherwise would be exposed. Smaller particles are not created by exposing the solvent to higher and higher agitation and/or shear forces. The microparticle size is determined instead by nonstress parameters such as polymer concentration, viscosity, solvent/nonsolvent miscibility and solvent/nonsolvent volumetric ratios. The invention also provides micron and even submicron sized polymer particles. It provides the additional advantage of producing those particles with minimal losses of the material to be encapsulated. Again, minimizing losses has important implications on productions costs.

It readily will be understood that the process of the present invention is essentially a single step process, which is scalable. Automation therefore will be straightforward.

An additional advantage of the invention is the ability to produce microparticles characterized by a homogenous size distribution. Such microparticles will have well defined, predictable properties.

According to one aspect of the invention, a method for microencapsulating an agent to form a microencapsulated product is provided. A polymer is dissolved in an effective amount of a solvent. The agent is also dissolved or dispersed in the effective amount of the solvent. The polymer, the agent and the solvent together form a mixture having a continuous phase, wherein the solvent is the continuous phase. The mixture is introduced into an effective amount of a nonsolvent to cause the spontaneous formation of the microencapsulated product, wherein the solvent and the nonsolvent are miscible and 0<$\delta$ solvent –$\delta$ nonsolvent <6.

The microencapsulated product that results can take on a variety of characteristics, depending upon the agents, polymers, solvents and nonsolvents employed and the various conditions of the phase inversion. These parameters may be adjusted so that the microencapsulated product consists of microparticles having an average particle size of between 10 nanometers and 10 microns. The average particle size, of course, may be adjusted within this range, for example to between 50 nanometers and 5 microns or between 100 nanometers and 1 micron.

The particle size is influenced by the solvent:nonsolvent volume ratio, which preferably is between 1:50 and 1:200. A working range for the solvent:nonsolvent volume ratio is between 1:40 and 1:1,000,000.

The polymer concentration in the solvent also can affect the microparticle size. It is preferred that the polymer concentration be between 0.1% weight/volume to 5% weight/volume, although higher polymer concentrations such as 10%, 20% or even higher are possible depending, inter alia, on the viscosity of the polymer solution, the molecular weight of the polymer and the miscibility of the solvent and nonsolvent.

The viscosity of the polymer/solvent solution also can affect particle size. It preferably is less than 2 centipoise, although higher viscosities such as 3, 4, 6 or even higher centipoise are possible depending upon adjustment of other parameters.

The molecular weight of the polymer also can affect particle size. The preferred range is 2 kDa–50 kDa, although a working range is 1 kDa–50 kDa. Other polymer sizes are possible depending upon adjustment of the other parameters.

It further is possible to influence particle size through the selection of characteristics of the solvent and nonsolvent. For example, hydrophilic solvent/nonsolvent pairs affect particle size relative to hydrophobic solvent/nonsolvent pairs.

The foregoing parameters, alone or in any combination, are considered important aspects of the invention.

According to another aspect of the invention, a method for microencapsulating an agent to form a microencapsulated product is provided. A polymer is dissolved in a solvent at a concentration of between 0.25 and 10% weight per volume. An agent also is dissolved or is dispersed in the solvent. The polymer, agent and solvent form a mixture, wherein the viscosity of the mixture is less than 3.5 centipoise. The mixture is introduced into a nonsolvent, wherein the volume ratio of the solvent:nonsolvent is at least 1:40, to cause the spontaneous formation of the microencapsulated product, wherein the solvent and the nonsolvent are miscible and wherein $0 < \delta$ solvent $-\delta$ nonsolvent $< 6$. Preferably, the polymer concentration is between 0.5 and 5% weight/volume, the viscosity is less than 2 centipoise, and the solvent:nonsolvent ratio is between 1:50 and 1:200.

According to another aspect of the invention, microparticles are provided. The microparticles are produced by the processes described above. It is believed that the processes of the invention result in products that have different physical characteristics than microparticles formed according to prior art methods.

The foregoing aspects of the invention as well as various objects, features and advantages are discussed in greater detail below.

DETAILED DESCRIPTION OF THE INVENTION

The invention involves the discovery that "phase inversion" of polymer solutions under certain conditions can bring about the spontaneous formation of discreet microparticles. The process, dubbed "phase inversion nanoencapsulation" or "PIN", differs from existing methods of encapsulation in that it is essentially a 1-step process, is nearly instantaneous, and does not require emulsification of the solvent. Under proper conditions, low viscosity polymer solutions can be forced to phase invert into fragmented spherical polymer particles when added to appropriate nonsolvents.

Phase inversion phenomenon has been applied to produce macro and microporous polymer membranes and hollow fibers. The basis for the formation of such membranes or fibers, as well as the process of the invention, depends upon the mechanism of microphase separation. A prevalent theory of microphase separation is based upon the belief that "primary" particles form of about 50 nm diameter, as the initial precipitation event resulting from solvent removal. As the process continues, primary particles are believed to collide and coalesce forming "secondary" particles with dimensions of approximately 200 nm, which eventually join with other particles to form the polymer matrix. An alternative theory, "nucleation and growth", is based upon the notion that a polymer precipitates around a core micellar structure (in contrast to coalescence of primary particles).

The fact that the present invention results in a very uniform size distribution of small particles forming at lower polymer concentrations without coalescing supports the nucleation and growth theory, while not excluding coalescence at higher polymer concentrations (e.g., greater than 10% weight per volume) where larger particles and even aggregates can be formed. (Solvent would be extracted more slowly from larger particles, so that random collisions of the partially-solvated spheres would result in coalescence and, ultimately, formation of fibrous networks.) By adjusting polymer concentration, polymer molecular weight, viscosity, miscibility and solvent:nonsolvent volume ratios, the interfibrillar interconnections characteristic of membranes using phase inversion are avoided, with the result being that microparticles are spontaneously formed. As will be seen from the examples below, as well as the following discussion, the foregoing parameters are interrelated and the adjustment of one will influence the absolute value permitted for another.

In the preferred processing method, a mixture is formed of the agent to be encapsulated, a polymer and a solvent for the polymer. The agent to be encapsulated may be in liquid or solid form. It may be dissolved in the solvent or dispersed in the solvent. The agent thus may be contained in microdroplets dispersed in the solvent or may be dispersed as solid microparticles in the solvent. The phase inversion process thus can be used to encapsulate a wide variety of agents by including them in either micronized solid form or else emulsified liquid form in the polymer solution.

The loading range for the agent within the microparticles is between 0.01–80% (agent weight/polymer weight). When working with nanospheres, an optimal range is 0.1–5% (weight/weight).

In general, the agent includes, but is not limited to, adhesives, gases, pesticides, herbicides, fragrances, antifoulants, dies, salts, oils, inks, cosmetics, catalysts, detergents, curing agents, flavors, foods, fuels, metals, paints, photographic agents, biocides, pigments, plasticizers, propellants and the like. The agent also may be a bioactive agent. The bioactive agent can be, but is not limited to: adrenergic agent; adrenocortical steroid; adrenocortical suppressant; aldosterone antagonist; amino acid; anabolic; analeptic; analgesic; anesthetic; anorectic; anti-acne agent; anti-adrenergic; anti-allergic; anti-amebic; anti-anemic; anti-anginal; anti-arthritic; anti-asthmatic; anti-atherosclerotic; antibacterial; anticholinergic; anticoagulant; anticonvulsant; antidepressant; antidiabetic; antidiarrheal; antidiuretic; antiemetic; anti-epileptic; antifibrinolytic; antifungal; antihemorrhagic; antihistamine; antihyperlipidemia; antihypertensive; antihypotensive; anti-infective; anti-inflammatory; antimicrobial; antimigraine; antimitotic; antimycotic, antinauseant, antineoplastic, antineutropenic, antiparasitic; antiproliferative; antipsychotic; antirheumatic; antiseborrheic; antisecretory; antispasmodic; antithrombotic; antiulcerative; antiviral; appetite suppressant; blood glucose regulator; bone resorption inhibitor; bronchodilator; cardiovascular agent; cholinergic; depressant; diagnostic aid; diuretic; dopaminergic agent; estrogen receptor agonist; fibrinolytic; fluorescent agent; free oxygen radical scavenger; gastrointestinal motility effector; glucocorticoid; hair growth stimulant; hemostatic; histamine H2 receptor antagonists; hormone; hypocholesterolemic; hypoglycemic; hypolipidemic; hypotensive; imaging agent; immunizing agent; immunomodulator; immunoregulator; immunostimulant; immunosuppressant; keratolytic; LHRH agonist; mood regulator; mucolytic; mydriatic; nasal decongestant; neuromuscular blocking agent; neuroprotective; NMDA antagonist; non-hormonal sterol derivative; plasminogen activator; platelet activating factor antagonist; platelet aggregation inhibitor; psychotropic; radioactive agent; scabicide; sclerosing agent; sedative; sedative-hypnotic; selective adenosine Al antagonist; serotonin antagonist; serotonin inhibitor; serotonin receptor antagonist; steroid; thyroid hormone; thyroid inhibitor; thyromimetic; tranquilizer; amyotrophic lateral sclerosis agent; cerebral ischemia agent; Paget's disease agent; unstable angina agent; vasoconstrictor; vasodilator; wound healing agent; xanthine oxidase inhibitor.

Bioactive agents include immunological agents such as allergens (e.g., cat dander, birch pollen, house dust, mite, grass pollen, etc.) and antigens from pathogens such as viruses, bacteria, fungi and parasites. These antigens may be in the form of whole inactivated organisms, peptides, proteins, glycoproteins, carbohydrates or combinations thereof. Specific examples of pharmacological or immunological agents that fall within the above-mentioned categories and that have been approved for human use may be found in the published literature.

The agent is added to the polymer solvent, preferably after the polymer is dissolved in the solvent. The solvent is any suitable solvent for dissolving the polymer. Typically the solvent will be a common organic solvent such as a halogenated aliphatic hydrocarbon such as methylene chloride, chloroform and the like; an alcohol; an aromatic hydrocarbon such as toluene; a halogenated aromatic hydrocarbon; an ether such as methyl t-butyl; a cyclic ether such as tetrahydrofuran; ethyl acetate; diethylcarbonate; acetone; or cyclohexane. The solvents may be used alone or in combination. The solvent chosen must be capable of dissolving the polymer, and it is desirable that the solvent be inert with respect to the agent being encapsulated and with respect to the polymer.

The polymer may be any suitable microencapsulation material including, but not limited to, nonbioerodable and bioerodable polymers. Such polymers have been described in great detail in the prior art. They include, but are not limited to: polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethylmethacrylate), poly(butylmethacrylate), poly(isobutylmethacrylate), poly(hexlmethacrylate), poly(isodecylmethacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene poly(ethylene glycol), poly(ethylene oxide), poly(ethylene terephthalate), poly(vinyl alcohols), poly(vinyl acetate, poly vinyl chloride polystyrene and polyvinylpryrrolidone.

Examples of preferred non-biodegradable polymers include ethylene vinyl acetate, poly(meth) acrylic acid, polyamides, copolymers and mixtures thereof.

Examples of preferred biodegradable polymers include synthetic polymers such as polymers of lactic acid and glycolic acid, polyanhydrides, poly(ortho)esters, polyurethanes, poly(butic acid), poly(valeric acid), poly(caprolactone), poly(hydroxybutyrate), poly(lactide-co-glycolide) and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. The foregoing materials may be used alone, as physical mixtures (blends), or as co-polymers. The most preferred polymers are polyesters, polyanhydrides, polystyrenes and blends thereof.

Particularly preferred are bioadhesive polymers. A bioadhesive polymer is one that binds to mucosal epithelium under normal physiological conditions. Bioadhesion in the gastrointestinal tract proceeds in two stages: (1) viscoelastic deformation at the point of contact of the synthetic material into the mucus substrate, and (2) formation of bonds between the adhesive synthetic material and the mucus or the epithelial cells. In general, adhesion of polymers to tissues may be achieved by (i) physical or mechanical bonds, (ii) primary or covalent chemical bonds, and/or (iii) secondary chemical bonds (i.e., ionic). Physical or mechanical bonds can result from deposition and inclusion of the adhesive material in the crevices of the mucus or the folds of the mucosa. Secondary chemical bonds, contributing to bioadhesive properties, consist of dispersive interactions (i.e., Van der Waals interactions) and stronger specific interactions, which include hydrogen bonds. The hydrophilic functional groups primarily responsible for forming hydrogen bonds are the hydroxyl and the carboxylic groups. Numerous bioadhesive polymers are discussed in that application. Representative bioadhesive polymers of particular interest include bioerodible hydrogels described by H. S. Sawhney, C. P. Pathak and J. A. Hubell in *Macromolecules.* 1993, 26:581–587, the teachings of which are incorporated herein, polyhyaluronic acids, casein, gelatin, glutin, polyanhydrides, polyacrylic acid, alginate, chitosan, poly (methyl methacrylates), poly(ethyl methacrylates), poly butylmethacrylate), poly(isobutylmethacrylate), poly (hexlmethacrylate), poly(isodecl methacrylate), poly(lauryl methacrylate), poly(phenyl methacrylate), poly(methyl acrylate), poly(isopropyl acrylate), poly(isobutyl acrylate), and poly(octadecl acrylate). Most preferred is poly(fumaric-co-sebacic)acid.

Polymers with enhanced bioadhesive properties can be provided wherein anhydride monomers or oligomers are incorporated into the polymer. The oligomer excipients can be blended or incorporated into a wide range of hydrophilic and hydrophobic polymers including proteins, polysaccharides and synthetic biocompatible polymers. Anhydride oligomers may be combined with metal oxide particles to improve bioadhesion even more than with the organic additives alone. Organic dyes because of their electronic charge and hydrophobicity/hydrophilicity can either increase or decrease the bioadhesive properties of polymers when incorporated into the polymers. The incorporation of oligomer compounds into a wide range of different polymers which are not normally bioadhesive dramatically increases their adherence to tissue surfaces such as mucosal membranes.

As used herein, the term "anhydride oligomer" refers to a diacid or polydiacids linked by anhydride bonds, and having carboxy end groups linked to a monoacid such as acetic acid by anhydride bonds. The anhydride oligomers have a molecular weight less than about 5000, typically between about 100 and 5000 daltons, or are defined as including between one to about 20 diacid units linked by anhydride bonds. In one embodiment, the diacids are those normally found in the Krebs glycolysis cycle. The anhydride oligomer compounds have high chemical reactivity.

The oligomers can be formed in a reflux reaction of the diacid with excess acetic anhydride. The excess acetic anhydride is evaporated under vacuum, and the resulting oligomer, which is a mixture of species which include between about one to twenty diacid units linked by anhydride bonds, is purified by recrystallizing, for example from toluene or other organic solvents. The oligomer is collected by filtration, and washed, for example, in ethers. The reaction produces anhydride oligomers of mono and poly acids with terminal carboxylic acid groups linked to each other by anhydride linkages.

The anhydride oligomer is hydrolytically labile. As analyzed by gel permeation chromatography, the molecular weight may be, for example, on the order of 200–400 for fumaric acid oligomer (FAPP) and 2000–4000 for sebacic acid oligomer (SAPP). The anhydride bonds can be detected by Fourier transform infrared spectroscopy by the characteristic double peak at 1750 $cm_{-1}$ and 1820 $cm^{-1}$, with a corresponding disappearance of the carboxylic acid peak normally at 1700 $cm^{-1}$.

In one embodiment, the oligomers may be made from diacids described for example in U.S. Pat. No. 4,757,128 to Domb et al., U.S. Pat. No. 4,997,904 to Domb, and U.S. Pat. No. 5,175,235 to Domb et al., the disclosures of which are incorporated herein by reference. For example, monomers such as sebacic acid, bis(p-carboxy-phenoxy)propane, isophathalic acid, fumaric acid, maleic acid, adipic acid or dodecanedioic acid may be used.

Organic dyes, because of their electronic charge and hydrophilicity/hydrophobicity, may alter the bioadhesive properties of a variety of polymers when incorporated into the polymer matrix or bound to the surface of the polymer. A partial listing of dyes that affect bioadhesive properties include, but are not limited to: acid fuchsin, alcian blue, alizarin red s, auramine o, azure a and b, Bismarck brown y, brilliant cresyl blue ald, brilliant green, carmine, cibacron blue 3GA, congo red, cresyl violet acetate, crystal violet, eosin b, eosin y, erythrosin b, fast green fcf, giemsa, hematoylin, indigo carmine, Janus green b, Jenner's stain, malachite green oxalate, methyl blue, methylene blue, methyl green, methyl violet 2b, neutral red, Nile blue a, orange II, orange G, orcein, paraosaniline chloride, phloxine b, pyronin b and y, reactive blue 4 and 72, reactive brown 10, reactive green 5 and 19, reactive red 120, reactive yellow 2,3, 13 and 86, rose bengal, safranin o, Sudan III and IV, Sudan black B and toluidine blue.

The working molecular weight range for the polymer is on the order of 1 kDa–150,000 kDa, although the optimal range is 2 kDa–50 kDa. The working range of polymer concentration is 0.01–50% (weight/volume), depending primarily upon the molecular weight of the polymer and the resulting viscosity of the polymer solution. In general, the low molecular weight polymers permit usage of a higher concentration of polymer. The preferred concentration range according to the invention will be on the order of 0.1%–10% (weight/volume), while the optimal polymer concentration typically will be below 5%. It has been found that polymer concentrations on the order of 1–5% are particularly useful according to the methods of the invention.

The viscosity of the polymer solution preferably is less than 3.5 centipoise and more preferably less than 2 centipoise, although higher viscosities such as 4 or even 6 centipoise are possible depending upon adjustment of other parameters such as molecular weight. It will be appreciated by those of ordinary skill in the art that polymer concentration, polymer molecular weight and viscosity are interrelated, and that varying one will likely affect the others.

The nonsolvent, or extraction medium, is selected based upon its miscibility in the solvent. Thus, the solvent and nonsolvent are thought of as "pairs". We have determined that the solubility parameter ($\delta(cal/cm^3)^{1/2}$) is a useful indicator of the suitability of the solvent/nonsolvent pairs. The solubility parameter is an effective protector of the miscibility of two solvents and, generally, higher values indicate a more hydrophilic liquid while lower values represent a more hydrophobic liquid (e.g., $\delta_i$ water=23.4(cal/$cm^3)^{1/2}$ whereas $\delta_i$hexane=7.3 $(cal/cm^3)^{1/2}$). We have determined that solvent/nonsolvent pairs are useful where $0<\delta$ solvent $-\delta$ nonsolvent $<6(cal/cm^3)^{1/2}$. Although not wishing to be bound by any theory, an interpretation of this finding is that miscibility of the solvent and the nonsolvent is important for formation of precipitation nuclei which ultimately serve as foci for particle growth. If the polymer solution is totally immiscibile in the nonsolvent, then solvent extraction does not occur and nanoparticles are not formed. An intermediate case would involve a solvent/nonsolvent pair with slight miscibility, in which the rate of solvent removal would not be quick enough to form discreet microparticles, resulting in aggregation of coalescence of the particles.

It, surprisingly, was discovered that nanoparticles generated using "hydrophilic" solvent/nonsolvent pairs (e.g., a polymer dissolved in methylene chloride with ethanol as the nonsolvent) yielded approximately 100% smaller particles than when "hydrophobic" solvent/nonsolvent pairs were used (e.g., the same polymer dissolved in methylene chloride with hexane as the nonsolvent).

Similarly, it was discovered, surprisingly, that the solvent-:nonsolvent volume ratio was important in determining whether microparticles would be formed without particle aggregation or coalescence. A suitable working range for solvent:nonsolvent volume ratio is believed to be 1:40–1:1,000,000. An optimal working range for the volume ratios for solvent:nonsolvent is believed to be 1:50–1:200 (volume per volume). Ratios of less than approximately 1:40 resulted in particle coalescence, presumably due to incomplete solvent extraction or else a slower rate of solvent diffusion into the bulk nonsolvent phase.

It will be understood by those of ordinary skill in the art that the ranges given above are not absolute, but instead are interrelated. For example, although it is believed that the solvent:nonsolvent minimum volume ratio is on the order of 1:40, it is possible that microparticles still might be formed at lower ratios such as 1:30 if the polymer concentration is extremely low, the viscosity of the polymer solution is extremely low and the miscibility of the solvent and non-solvent is high. Thus, as used in connection with the claims, the polymer is dissolved in an effective amount of solvent, and the mixture of agent, polymer and polymer solvent is introduced into an effective amount of a nonsolvent, so as to produce polymer concentrations, viscosities and solvent-:nonsolvent volume ratios that cause the spontaneous and virtually instantaneous formation of microparticles.

As will be seen from the examples below, a variety of polymers have been tested in the methods of the invention, including polyesters such as poly(lactic acid), poly(lactide-co-glycolide) in molar ratios of 50:50 and 75:25; polycaprolactone; polyanhydrides such as poly(fumaric-co-sabacic) acid or P(FA:SA) in molar ratios of 20:80 and 50:50; poly(carboxyphenoxypropane-co-sebacic) acid or P(CPP:SA) in molar ratio of 20:80; and polystyrenes or PS.

Nanospheres and microspheres in the range of 10 nm to 10 µm have been produced according to the methods of the invention. Using initial polymer concentrations in the range of 1–2% (weight/volume) and solution viscosities of 1–2 centipoise, with a "good" solvent such as methylene chloride and a strong non-solvent such as petroleum ether or hexane, in an optimal 1:100 volume ratio, generates particles with sizes ranging from 100–500 nm. Under similar conditions, initial polymer concentrations of 2–5% (weight/volume) and solution viscosities of 2–3 centipoise typically produce particles with sizes of 500–3,000 nm. Using very low molecular weight polymers (less than 5 kDa), the viscosity of the initial solution may be low enough to enable the use of higher than 10% (weight/volume) initial polymer concentrations which generally result in microspheres with sizes ranging from 1–10 µm. In general, it is likely that concentrations of 15% (weight/volume) and solution viscosities greater than about 3.5 centipoise discreet microspheres will not form but, instead, will irreversibly coalesce into intricate, interconnecting fibrilar networks with micron thickness dimensions.

It is noted that only a limited number of microencapsulation techniques can produce particles smaller than 10 microns, and those techniques are associated with significant losses of polymer, the material to be encapsulated, or both. This is particularly problematic where the active agent is an expensive entity such as certain medical agents. The present invention provides a method to produce nano to micro-sized particles with minimal losses. The described methods can result in product yields greater than 80% and encapsulation efficiencies as high as 100%.

The methods of the invention also can produce microparticles characterized by a homogeneous size distribution. Typical microencapsulation techniques produce heterogeneous size distributions ranging from 10 µm to mm sizes. Prior art methodologies attempt to control particle size by parameters such as stirring rate, temperature, polymer/suspension bath ratio, etc. Such parameters, however, have not resulted in a significant narrowing of size distribution. The present invention can produce, for example, nanometer sized particles which are relatively monodisperse in size. By producing a microparticle that has a well defined and less variable size, the properties of the microparticle such as when used for release of a bioactive agent can be better controlled. Thus, the invention permits improvements in the preparation of sustained release formulations for administration to subjects.

The invention also provides further methods for controlling the size of the four microspheres. This is particularly useful where the material to be encapsulated must first be dispersed in the solvent and where it would be undesirable to sonicate the material to be encapsulated. The mixture of the material to be encapsulated and the solvent (with dissolved polymer) can be frozen in liquid nitrogen and then lyophilized to disperse the material to be encapsulated in the polymer. The resulting mixture then can be redissolved in the solvent, and then dispersed by adding the mixture to the nonsolvent. This methodology was employed in connection with dispersing DNA, shown in the examples below.

As mentioned above, the methods of the invention can be, in many cases, carried out in less than five minutes in the entirety. It is typical that preparation time may take anywhere from one minute to several hours, depending on the solubility of the polymer and the chosen solvent, whether the agent will be dissolved or dispersed in the solvent and so on. Nonetheless, the actual encapsulation time typically is less than thirty seconds.

After formation of the microcapsules, they are collected by centrifugation, filtration, and the like. Filtering and drying may take several minutes to an hour depending on the quantity of material encapsulated and the methods used for drying the nonsolvent. The process in its entirety may be discontinuous or a continuous process.

Because the process does not require forming the solvent into an emulsion, it generally speaking may be regarded as a more gentle process than those that require emulsification. As a result, materials such as whole plasmids including genes under the control of promoters can be encapsulated without destruction of the DNA as a result of the emulsification process. Thus the invention particularly contemplates encapsulating materials such as plasmids, vectors, external guide sequences for RNAase P, ribozymes and other sensitive oligonucleotides, the structure and function of which could be adversely affected by aggressive emulsification conditions and other parameters typical of certain of the prior art processes.

Included below are several examples of the present invention and the novel products produced thereby. Most of these examples product microparticles ranging in size from 100 nanometers to 10 microns. Although illustrative of the advance in the art achieved by the present invention, it is expected that those skilled in polymer science and microencapsulation processes will, on the basis of these examples, be able to select appropriate polymers, solvents, nonsolvents, solution modifiers, excipients, diluents, encapsulants and so on to spontaneously form microparticles exhibiting desirable properties, including properties desirable for medical applications such as sustained release of bioactive compounds or oral delivery of drug compounds.

The following non-limiting examples describe the preparation of microspheres by the phase inversion method in which a polymer dissolved in a continuous phase solvent system coalesces into a solid macromolecular network in which the polymer is the continuous phase (Kestling, et. al., Materials Science of Synthetic Membranes, p. 132–164 (1985)). This event can be induced through several means: removal of solvent (e.g. by evaporation), addition of another species, addition of a non-solvent or addition to a non-solvent (wet process). In the latter, the polymer solution can be poured or extruded into a non-solvent bath. The method and materials of the present invention will be further understood by reference to these non-limiting Examples.

EXAMPLES

Example 1

Preparation of Microspheres by Phase Inversion Nanoencapsulation

Methods

A variety of polymers have been used to fabricate "PIN" nanospheres including: polyesters, such as poly(lactic acid) or PLA, poly(lactic-co-glycolide) or PLGA in molar ratios of 50:50 and 75:25, polycaprolactone or PLC; polyanhydrides, such as poly(fumaric-co-sebacic) acid or P(FA:SA) in molar ratios of 20:80 and 50:50 poly (carboxyphenoxypropane-co-sebacic) acid of P(CPP:SA) in molar ratio of 20:80; and polystyrenes or PS. Polymers with molecular weights ranging from 1–112,000 kDa have been successfully used to fabricate nanospheres (see Table 1 below). Unless otherwise indicated all reagents used were obtained from Sigma Chemical Company of St. Louis, Mo. or Aldrich Chemicals of Milwaukee, Wis.

Results

1. Preparation of a Drug Free Nanosphere 5 ml of 1% polyvinylphenol (w/v) (PVP, Polysciences, Inc.) in methylene chloride was rapidly added to 200 ml of petroleum ether without stirring. The mixture was immediately filtered and the resulting nanospheres were air dried on the filter paper.

The dried nanospheres were examined by scanning electron microscopy (SEM) (data not shown). The micrographs revealed a monodisperse preparation of distinct nanospheres ranging in size from 10 to 100 nm. The low size range of the nanospheres is characteristic of nanospheres formed using low concentrations of polymer (1–5% w/v).

2. Preparation of Microspheres (and Nanospheres) Including a Microencapsulated Fluorescent Low Molecular Weight, Hydrophilic Dye 5 ml of 5% polylactic acid-2 KDa (PLA) (Boehringer Ingleheim, Inc.) in methylene chloride (w/v) containing 0.1% (w/v) rhodamine 6 G (2.0% w/w) was added quickly to 200 ml of petroleum ether without stirring. The mixture was immediately filtered and the resulting microspheres were air dried on the filter paper.

A large batch of the same microspheres was formed by rapidly adding 100 ml of 5% PLA (w/v) in methylene chloride containing 0.1% (w/v) rhodamine 6 G to 4 liters of petroleum ether without stirring. This mixture was immediately filtered and the resulting microspheres were air dried on the filter paper.

Both sets of microspheres were examined by SEM and were found to consist of a monodisperse preparation of distinct microspheres. Both preparations of microspheres ranged in size from 0.5 to 5μ. The fluorescent dye was entrapped within the microspheres. Analysis of the polymer content of the microspheres, revealed that 4.9 gm of the original 5.0 gm of polymer was recovered, providing an overall yield recovery of 98%.

3. Preparation of Microspheres (and Nanospheres) With Microencapsulated Sodium Chloride Crystals 0.3 g of spray-dried NaCl, having an average particle size of 0.1–10μ, cubic morphology, was dispersed by probe sonication and stirred into 10 ml of 5% PLA (w/v) in methylene chloride. The salt loading was 37.5% w/w. This mixture was rapidly added to 400 ml of petroleum ether and immediately filtered. The resulting microspheres were air dried on the filter paper. In some experiments the resulting microspheres were incubated for 1.5 hours in 0.9% NaCl (w/v), washed with distilled water and air dried.

The untreated sodium chloride microspheres consisted of a monodispersed preparation of distinct microspheres ranging in size from 0.5 to 5μ, as determined by SEM. The salt crystals were entirely entrapped by the microspheres. No free cubic crystals of salt were observed in the preparation. SEM of the saline treated microspheres revealed that in some instances these microspheres had a sponge-like morphology, which may be useful for an ultrasound imaging agent.

4. Preparation of Microspheres Having a Diameter Greater Than 10μ, Using the Phase Inversion Method 5 ml of 10% PVP 9–11 KDa (Polysciences Inc) (w/v) in methylene chloride was rapidly added to 200 ml of petroleum ether without stirring. The mixture was immediately filtered and the resulting microspheres were air dried on filter paper.

Examination of the dried microspheres by SEM revealed that the microspheres consisted of discrete spherical particles in the size range of 2 to 20μ. The results suggest that microspheres prepared from low molecular weight polymers (less than 50 KDa) having concentrations between 5 and 10% (w/v) were larger in size (up to 20μ). Therefore, the resulting microsphere size can be controlled by manipulating the polymer concentration.

5. Preparation of Hydrophobic Protein Microspheres Coated With Bioadhesive Polymers by Phase Inversion A hydrophobic protein, such as zein F 4000 (prolamine), derived from corn, was dissolved with sodium salicylate in 70% ethanol (EtOH), such that the concentration of zein and sodium salicylate was 7% w/v to yield a 1:1 weight ratio. The solution was spray dried to produce microspheres in the range of 1 to 20μ, having an average diameter of 5 to 7μ. 200 mg of the zein microspheres were vortexed and briefly bath-sonicated in 2.5 ml of 10% poly(fumaric-co-sebacic acid) 20:80 6 KDa, (P(FA:SA) (synthesized according to the procedure of Domb and Langer, *Journal of Polymer Science*, v. 25, p3373–3386 (1987)) (w/v) in methylene chloride and rapidly added to 400 ml of petroleum ether without stirring. The mixture was immediately filtered and air dried on the filter paper.

The average diameter of the uncoated zein microspheres was determined to be 5 to 7μ by SEM and the average diameter of the coated microspheres was found to be greater than 30μ.

6. Microspheres Were Coated With Polymer to Produce Coated Microspheres Having a Diameter Greater Than 20 μm Using Phase Inversion 0.5 g of glass beads were vortexed and bath sonicated for 1 minute in 2 ml of 20% polycaprolactone 76 Kda (PCL) (Aldrich) (w/v). This mixture was drained and added to petroleum ether with vigorous shaking. The petroleum ether was drained and the beads were air dried.

SEM of the resultant air dried product indicated that the beads were uniformly coated with polymer. The surface texture of the coating was rough. Examination at a higher magnification revealed that the roughness was attributable to polymer spherulites, measuring 10–20μ in length.

7. The Use of Polymers Having Low Glass Transition Temperatures Produces Globular Aggregates Rather Than Microspheres 5 ml of 1% ethylene vinyl acetate 55 KDa (EVA) (Du Pont, Inc.) (w/v) in methylene chloride containing 0.1% (w/v) of rhodamine 6 G (10.0% w/w, encapsulant) was rapidly added to 200 ml of petroleum ether without stirring. The mixture was immediately filtered and the resulting composition was air dried on the filter paper. The dried composition was examined by SEM and found to be in the form of globular aggregates. The fluorescent dye was entrapped by the globular aggregates. The results indicate that polymers having low glass transition temperatures (i.e., below ambient) tend to coalesce during phase inversion.

Example 2

Drug Release Profile from Microspheres Created by Phase Inversion Nanoencapsulation 1. Release of Dicumarol From Dicumarol Containing Polyanhydride(FA:SA) (P(FA:SA)) Microspheres Dicumarol containing microspheres were formed by adding 0.1 g spray dried dicumarol (40% w/w) to 5 ml of 5% polyanhydride (FA:SA) 20:80 (w/v) in methylene chloride. The mixture was rapidly added to 100 ml of petroleum ether without stirring and immediately filtered. The resulting microspheres were washed with petroleum ether to remove loosely adherent drug on the surface of the microspheres and then air dried on the filter paper.

Aliquots of dicumarol containing microspheres, containing approximately 5 mg of dicumarol, were used in studies to examine the release of drug from the microsphere. 5 mg of spray dried dicumarol was used as a control. The dicumarol containing microspheres or the spray dried dicumarol were separately incubated in 10 ml of phosphate-buffered saline, pH 7.2 (PBS) at room temperature for 10 hours. Periodically, 100 $\mu$l samples of the incubation fluid were withdrawn and analyzed for dicumarol concentration using a UV spectrophotometric assay. The release of dicumarol from the encapsulated microspheres was at least ten-fold less than the control, spray dried drug after three hours.

2. Release of Small Highly Water Soluble Drug Can Be Optimized by Producing Microcapsules by the Phase Inversion Method Salicylic acid was encapsulated in PVP (1–7 KDa Polysciences) by spray drying a 1:1 ratio of 10% (w/v) solution of each component in acetone at 65° C. The particles were mixed with a 5% P(FA:SA) 20:80 solution (w/v) in methylene chloride so that the final loading of the drug was 16% (w/w) with respect to the P(FA:SA). 10 ml of this mixture was poured into 200 ml of petroleum ether. The resulting microspheres were collected by filtration and air dried.

Aliquots of PVP or P(FA:SA)-encapsulated-PVP microspheres containing approximately 40 mg of salicylic acid were incubated in 10 ml of phosphate-buffered saline, pH 7.2 (PBS) at room temperature for 10 hours. As a control, 40 mg of salicylic acid alone was subjected to the same conditions. Periodically, 100 $\mu$l samples of the incubation fluid were collected and analyzed for dicumarol concentration using a visible spectrophotometric assay. Although the release of salicylic acid from PVP-microspheres was not significantly different from the dissolution of stock salicylic acid, the release of salicylic acid from P(FA:SA) coated microspheres was observed to be markedly decreased. An improved linearity of drug release was also observed. SEM of the coated microspheres indicated that the beads were uniformly coated with polymer, and had a particle size of 10$\mu$. These results indicate that phase inversion encapsulation can produce controlled release of a small highly water soluble drug and also that multiple polymer systems can be used to optimize delivery of drugs by this method.

3. Emulsions of Proteins Can Be Released From Microspheres Produced by Phase Inversion Encapsulation 0.5 ml of 20 mg FITC-BSA/ml (Sigma Chemical Co.) of phosphate-buffered saline (PBS) was re-suspended in 10 ml of 1% PLA 2 KDa (w/v) in methylene chloride to yield a protein loading of 9.1% (w/w). The mixture was probe-sonicated for three cycles of 10 seconds duration and quickly poured into 400 ml of petroleum ether. The resulting microspheres were filtered and air dried.

11.0 mg of the microspheres were incubated in 5 ml of PBS pH 7.2 at 37° C. Periodically, 50 $\mu$l samples of the incubation fluid were collected and analyzed for FITC-BSA using a visible spectrophotometric assay. The results of the assay indicated that the entire loading of the encapsulant was released into the incubation fluid within 30 minutes. These results suggest that the phase inversion encapsulation process may be used to entrap proteins, and that these emulsions of proteins in microspheres are rapidly released.

4. Release of Insulin From Nanospheres Composed of PLA and Poly (Fumaric Acid)

Micronized zinc insulin was incorporated into a 5% (w/v) polymer solution of a 4:1 blend of PLA 24 KDa and poly(fumaric acid) in methylene chloride at a loading of 4.4+/−0.7% (w/w). This mixture was dispersed into petroleum ether (1:100 solvent/nonsolvent volume ratio) and the resulting nanospheres were collected by filtration and air dried.

Insulin release from the nanospheres was studied over a 22 hour time period. After 1 hour, approximately 24 % of the total insulin was released and at the end of 5 hours, nearly 45% of the drug had released form the nanospheres. The rate of release of insulin slowed down between 5 and 22 hours. At the end of the experiment 53% of the initial loading remained encapsulated in the nanospheres.

Example 3

Microspheres Produced by Phase Inversion Encapsulation Exhibit Enhanced Bioavailability of Encapsulated Drugs In Vivo 1. Oral Delivery of Microparticles Studies were conducted to determine the fate of orally administered P(FA:SA)20:80 microparticles. The microparticles contained rhodamine and had a particle size range of between 0.1 and 1.0 micrometers. Rats were fed a single dose of 30 mg of such microparticles. As early as one hour posted-feeding of a single dose, microparticles were observed to traverse the mucosal epithelium by passing between absorptive cells (paracellular route). In addition, microparticles were seen crossing through follicle associated epithelium (FAE) and into the Peyer's patches. After three and six hours, an even greater number of microparticles were seen between epithelial cells and in the Peyer's patches. Focal areas demonstrated massive amounts of non-selective uptake, by both absorptive cells and Peyer's patches. Liver samples showed large numbers of nanospheres with apparently normal looking hepatocytes. Spleen sections also showed nanospheres, but fewer than in the liver. At twelve hours, large numbers spheres were still observed in between villous epithelial cells and in the Peyer's patches. Similar sections were observed even at twenty-four hours post-feeding.

This experiment showed extensive uptake of microparticles extending over at least twenty-four hours, following a single oral dose. Microparticles apparently crossed the epithelial boundary by passing in between cells. The observed uptake did not seem to be limited to the FAE overlying the Peyer's patches; uptake occurred diffusely by absorptive epithelium as well as FAE.

Transmission electron microscopy experiments using electron-opaque tracers such as micronized ferric oxide or 5 nm colloidal gold that had been microencapsulated with bioadhesive P(FASA) 20:80 were also conducted. The findings demonstrated that nanospheres in great number were indeed being taken up by absorptive epithelial cells lining the small intestine. In a typical thin section of an absorptive cell, up to one hundred nanospheres could be counted. While the results of light microscopy indicated a paracellular means of entry, these electron micrographs showed many microparticles within cells. The mechanism of entry is not known although several particles were occasionally observed in clear "endocytotic" vesicles located directly beneath the terminal web region in proximity to the apical microvillous border. The range of particle sizes observed in the cytoplasm of cells was 40–120 nm, well below the resolution of normal light optics and therefore undetectable by light microscopy. Nanoparticles were visualized in the cytoplasm, inside membranous profiles of the endoplasmic reticulum and Golgi apparatus and generally in the supranuclear (apical) portion of the absorptive cell. Occasionally, nanoparticles were seen near the basal aspects of the cell. Spheres were often found near the lateral borders of the cell, in the intracellular spaces and in close apposition to the tight junctions. These findings suggest that translocation of nanospheres via the transcellular route occurred in addition to paracellular movement.

2. Oral Delivery of Insulin

Insulin was encapsulated in P(FA)-PLGA(50:50) polymer blends using the phase inversion nanoencapsulation methods. After measuring fasting blood glucose levels, fasted rats were injected subcutaneously with an initial glucose load and then fed either a suspension of nanospheres containing 20 IU zinc-insulin (micronized FeO was included an electron dense tracer) in saline or else sham fed saline only. Blood glucose levels (BGL) were assayed at intervals after feeding.

The controls showed the expected response to the glucose load. BGL rose by 40 mg/dL after three hours and then slowly started to return towards baseline. In contrast, animals fed the encapsulated insulin formulation had consistently lower blood glucose levels than the control animals at three of the four time points that were sampled. After 1.5 hours, the BGL was 20 mg/dL below baseline compared to 30 mg/dL above baseline for control animals. At three hours the BGL of the nanoparticle treated animals rose to 20 mg/dL above baseline compared to a 40 mg/dL rise for the control animals (not statically different). At four hours, the BGL of the nanoparticle-fed animals was nearly 30 mg/dL below baseline, compared to a BGL of 20 mg/dL above base line for the control animals. After five hours, the glucose levels of the test group were lower than at four hours, while the levels of the control animals were still 35 mg/dL above baseline. Because the animals fed the encapsulated insulin preparation were better able to regulate the glucose load, it is clear that the insulin was not harmed by the encapsulation method, that the insulin survived the environment of the stomach, the insulin crossed the intestinal barrier and the insulin was released from the nanoparticles in a bioactive form. A widespread distribution of insulin-loaded nanospheres also was observed. The spheres were observed in great numbers, traversing the mucosal epithelium in the small intestine, in the Peyer's patches, in the lamina propria, in the lacteals and in the blood vessels of the gut wall. Nanoparticles also were observed in spleen and other tissue samples. Thus, systemic delivery of both insulin and nanoparticles was demonstrated.

3. Encapsulation and Oral Delivery of Dicumarol

Dicumarol containing microspheres were produced as described above in Example 2, subsection 1. Equal doses of dicumarol, spray dried dicumarol and polyanhydride (FA:SA) 20:80 encapsulated dicumarol (25 mg drug/kg body weight) suspended in 1.5 ml maple syrup were fed to catheterized rats (250–350 g). Blood samples were taken at regular intervals and serum was assayed for dicumarol concentrations using a UV spectrophotometric method.

The results of the in vivo studies indicate that the polyanhydride (FA:SA) microcapsule formulation had significantly increased bioavailability compared to the unencapsulated formulations, including the micronized drug. At 12 hours post-feeding, the serum concentrations for the polyanhydride (FA:SA) formulations were significantly higher than for the controls. At 48 hours post-feeding, the serum levels of dicumarol in the controls had returned to baseline, while those animals fed the bioadhesive polyanhydride formulation had detectable drug concentrations for at least 72 hours.

TABLE 1

ORAL BIOAVAILABILITY OF DICUMAROL

|  | STOCK DICUMAROL CONTROL | SPRAY DICUMAROL CONTROL | P(FA:SA) 20:80 "PIN" ENCAPSULATED DICUMAROL |
|---|---|---|---|
| C MAX (ug/ml) | 11.53 ± 1.10* | 17.94 ± 1.22 | 18.63 ± 1.76* |
| T MAX(hrs) | 9.87 ± 1.76 | 9.42 ± 1.36 | 10.61 ± 0.02 |
| t ½(half life) (hrs) | 18.25 ± 3.30 | 16.21 ± 0.87 | 17.92 ± 0.41 |
| AUC (area under curve) (ug/ml - hrs) | 171.48 ± 33.16 | 232.10 ± 19.20≠ | 363.59 ± 70.95≠ |

*= Significantly different at p < .03
≠= Significantly different at p < .005
(means ± std error)

These results indicate that phase inversion encapsulation of drugs in bioadhesive formulations, such as the polyanhydride (FA:SA) can increase bioavailability.

4. Incorporation of DNA Into Polymeric Nanospheres by Phase Inversion

This example provides a description of the incorporation of plasmid DNA into poly(fumaric acid:sebacic acid) 20:80 (P(FA:SA)) using a phase inversion technique.

Materials. P(FA:SA) 20:80 (synthesized by a method of A. Domb & R. Langer, Journal of Polymer Science, 1987, v. 25, p. 3373–3386), a reporter plasmid pCMV/βgal (Clonetech), methylene chloride (Fisher) and petroleum ether (Fisher) were used to construct the nanospheres.

Methods. 200 mg of P(FA:SA) in methylene chloride (1% wt/vol) is vortexed (30 sec) with 2 mg of pCMV/βgal in distilled water (1 mg/ml), frozen in liquid nitrogen and lyophilized overnight to disperse the DNA in the polymer. The purpose of this step was to reduce the particulate size and prevent aggregation of the DNA. DNA present in the disperse phase of the emulsion would not be able to aggregate due to the physical separation induced by the continuous polymer phase. The resulting mixture was redissolved in 2 ml of methylene chloride, poured into 200 ml of petroleum ether and filtered to recover microspheres encapsulating the DNA.

Results. Polymer nanoparticles produced using this technique were analyzed to determine whether DNA was encapsulated within the nanoparticles. Plasmid DNA was extracted from the nanoparticles and subjected to agarose gel electrophoresis. The results indicate that DNA was encapsulated without degradation. Thus, the phase inversion technique can be used to incorporate very large intact molecular weight plasmid DNA ($7.2 \times 10^6$ Daltons) in biodegradable nanoparticles.

Example 4

Processing Parameters

A variety of polymers, solvents, viscosities, non-solvents, drugs, and concentrations were tested in phase inversion experiments. Table 3 summarizes the results of many of these tests.

Each of the foregoing patents, patent applications and references is herein incorporated by reference in its entirety. Having described the presently preferred embodiments, in accordance with the present invention, it is believed that other modifications, variations and changes will be suggested to those skilled in the art in view of the teachings set forth herein. It is, therefore, to be understood that all such variations, modifications, and changes are believed to fall within the scope of the present invention as defined by the appended claims.

Those of ordinary skill in the art will readily ascertain numerous equivalents of the foregoing examples. Such equivalents are intended to be embraced by the following claims.

What we claim is:

1. A method for microencapsulating an agent to form a microencapsulated product, comprising:

dissolving a polymer in an effective amount of a solvent,

TABLE 3

| Polymer | MW | Concentration | Viscosity | Solvent | Non-Solvent | Drug | Concentration | Product |
|---|---|---|---|---|---|---|---|---|
| polystyrene | 2K | 5% | | $MeCl_2$ | pet ether | rhodamine | 0.1% | |
| polystyrene | 2K | 10% | | $MeCl_2$ | pet ether | rhodamine | 0.1% | |
| polystyrene | 50K | 1% | | $MeCl_2$ | pet ether | none | — | |
| polystyrene | 50K | 1% | | $MeCl_2$ | pet ether | rhodamine | 0.1% | 1–5 μm |
| polystyrene | 50K | 3% | | $MeCl_2$ | pet ether | rhodamine | 0.1% | |
| polystyrene | 50K | 5% | | $MeCl_2$ | pet ether | rhodamine | 0.1% | 500 nm - 2 μm |
| polystyrene | 50K | 10% | | $MeCl_2$ | pet ether | rhodamine | 0.1% | 1–4 μm |
| polystyrene | 50K | 15% | | $MeCl_2$ | pet ether | rhodamine | 0.1% | 1–10 μm & aggr |
| polystyrene | 50K | 20% | | $MeCl_2$ | pet ether | rhodamine | 0.1% | large aggregate |
| polystyrene | 50K | 1% | | $MeCl_2$ | ethanol | rhodamine | 0.1% | |
| polystyrene | 50K | 5% | | $MeCl_2$ | ethanol | rhodamine | 0.1% | <100 nm |
| polystyrene | 50K | 10% | | $MeCl_2$ | ethanol | rhodamine | 0.1% | <100 nm - 3 μm |
| polycaprolactone | 72K | 1% | 3.188 | $MeCl_2$ | pet ether | rhodamine | 0.1% | 1–3 μm |
| polycaprolactone | 72K | 5% | 7.634 | $MeCl_2$ | pet ether | rhodamine | 0.1% | 1–3 μm large aggr |
| polycaprolactone | 112K | 1% | 4.344 | $MeCl_2$ | pet ether | rhodamine | 0.1% | 500 nm - 5 μm |
| polycaprolactone | 112K | 5% | | $MeCl_2$ | ethanol | rhodamine | 0.1% | Large aggregate |
| polyvinylphenol | 1.5–7K | 1% | | acetone | pet ether | none | — | 250 nm - 1 μm |
| polyvinylphenol | 1.5–7K | 5% | | acetone | pet ether | none | — | |
| polyvinylphenol | 1.5–7K | 10% | | " acetone | pet ether | none | — | |
| polyvinylphenol | 9–11K | 1% | | acetone | pet ether | none | — | 100 nm - 2 μm |
| polyvinylphenol | 9–11K | 5% | | acetone | pet ether | none | — | 250 nm - 2.5 μm |
| polyvinylphenol | 9–11K | 10% | | acetone | pet ether | none | — | 500 nm - 10 μm |
| polylactic acid | 2K | 1% | 0.876 | $MeCl_2$ | pet ether | rhodamine | 0.1% | 100 nm |
| polylactic acid | 2K | 5% | 1.143 | $MeCl_2$ | pet ether | rhodamine | 0.1% | 500 nm - 2 μm |
| polylactic acid | 2K | 10% | 2.299 | $MeCl_2$ | pet ether | rhodamine | 0.1% | 1–10 μm brittle |
| polylactic acid | 24K | 1% | 1.765 | $MeCl_2$ | pet ether | rhodamine | 0.1% | 100 nm |
| polylactic acid | 24K | 5% | 2.654 | $MeCl_2$ | pet ether | rhodamine | 0.1% | 500 nm - 1 μm |
| polylactic acid | 24K | 10% | 3.722 | $MeCl_2$ | pet ether | rhodamine | 0.1% | 10 μm aggr |
| polylactic acid | 40–100K | 1% | 2.299 | $MeCl_2$ | pet ether | rhodamine | 0.1% | |
| polylactic acid | 40–100K | 5% | 2.832 | $MeCl_2$ | pet ether | rhodamine | 0.1% | |
| polylactic acid | 40–100K | 10% | 6.122 | $MeCl_2$ | pet ether | rhodamine | 0.1% | |
| polylactic acid | 100K | 1% | 2.566 | $MeCl_2$ | pet ether | rhodamine | 0.1% | 100 nm |
| polylactic acid | 100K | 5% | 4.433 | $MeCl_2$ | pet ether | rhodamine | 0.1% | 500 nm - 2 μm aggr |
| polylactic acid | 100K | 10% | 8.256 | $MeCl_2$ | pet ether | rhodamine | 0.1% | film/aggr |
| ethylenevinyl acetate | 55K | 1% | | $MeCl_2$ | pet ether | rhodamine | 0.1% | Globular strands |
| ethylenevinyl acetate | 55K | 5% | | $MeCl_2$ | pet ether | rhodamine | 0.1% | coalesced strands |
| ethylenevinyl acetate | 55K | 10% | | $MeCl_2$ | pet ether | rhodamine | 0.1% | continuous sheet |
| PAN/PVC | | 1% | 2.566 | acetone | pet ether | none | — | coarse 1–20 μm |
| PAN/PVC | | 5% | 15.903 | acetone | pet ether | none | — | 100 μm aggr |

Each of the foregoing patents, patent applications and references is herein incorporated by reference in its entirety. Having described the presently preferred embodiments, in accordance with the present invention, it is believed that other modifications, variations and changes will be suggested to those skilled in the art in view of the teachings set forth herein. It is, therefore, to be understood that all such variations, modifications, and changes are believed to fall within the scope of the present invention as defined by the appended claims.

dissolving or dispersing said agent in said effective amount of said solvent, wherein said polymer, said agent and said solvent form a mixture having a continuous phase and wherein the solvent is said continuous phase, and introducing said mixture into an effective amount of a nonsolvent to cause the spontaneous formation of said microencapsulated product, wherein said solvent and said nonsolvent are miscible and 0<δ solvent −δ nonsolvent <6 wherein the nonsolvent and solvent are used in effective amounts, wherein the effective amount of nonsolvent and solvent is an effective amount when the solvent:nonsolvent volume ratio is between 1:40 and 1:1,000,000.

2. The method of claim 1 wherein the agent is dissolved in the solvent.

3. The method of claim 1 wherein the agent is dispersed as solid microparticles in the solvent.

4. The method of claim 1 wherein the agent is contained in microdroplets dispersed in the solvent.

5. The method of claim 1 wherein the agent is a liquid.

6. The method of claim 1 wherein the agent is a bioactive agent.

7. The method of claim 1 wherein the microencapsulated product consists of microparticles having an average particle size of between 10 nanometers and 10 microns.

8. The method of claim 1 wherein the microencapsulated product consists of microparticles having an average particle size between 100 nanometers and 5 microns.

9. The method of claim 1 wherein the microencapsulated product consists of microparticles having an average particle size of between 100 nanometers and 1 micron.

10. The method of claim 1 further comprising separating the microencapsulated product from the nonsolvent.

11. The method of claim 1 wherein the solvent:nonsolvent volume ratio is between 1:50 and 1:200.

12. The method of claim 1 wherein the concentration of the polymer in the solvent is less than 20% weight per volume.

13. The method of claim 1 wherein the concentration of the polymer in the solvent is less than 10% weight per volume.

14. The method of claim 1 wherein the concentration of the polymer in the solvent is less than 5% weight per volume.

15. The method of claim 1 wherein the concentration of the polymer in the solvent is between 1 and 5% weight per volume.

16. The method of claim 1 wherein the mixture has a viscosity less than 6 centepoise.

17. The method of claim 1 wherein the mixture has a viscosity less than 4 centepoise.

18. The method of claim 1 wherein the mixture has a viscosity less than 3 centepoise.

19. The method of claim 1 wherein the mixture has a viscosity less than 2 centepoise.

20. The method of claim 1 wherein the solvent and nonsolvent are hydrophilic pairs.

21. The method of claim 1 wherein the concentration of polymer in the solvent is less than 10% weight per volume and wherein the viscosity of the solvent is less than 3.5 centepoise.

22. The method of claim 1 wherein the solvent:nonsolvent ratio is greater than 1:40 and wherein the viscosity of the mixture is less than 3.5 centepoise.

23. A method for microencapsulating an agent to form a microencapsulated product, comprising:

dissolving a polymer in a solvent at a concentration of less than 10% weight/volume, dissolving or dispersing said agent in said solvent, wherein said polymer, said agent and said solvent form a mixture having a viscosity of less than 3.5 centipoise, and introducing said mixture into a nonsolvent, wherein the volume ratio of solvent:nonsolvent is at least 1:40, to cause the spontaneous formation of said microencapsulated product, wherein said solvent and said nonsolvent are miscible and $0<\delta$ solvent $-\delta$ nonsolvent $<6$.

24. The method of claim 23 wherein the concentration of the polymer in the solvent is between 0.5 and 5% weight per volume, and wherein the volume ration of solvent:nonsolvent is between 1:50 and 1:200.

25. A method for microencapsulating an agent to form a microencapsulated product, comprising:

dissolving a polymer in an effective amount of a solvent, dissolving or dispersing an agent in the effective amount of the solvent by freezing the mixture of the solvent, the polymer, and the agent to form a frozen mixture and drying by vacuum the frozen mixture, wherein the polymer, the agent and the solvent in the frozen mixture have a continuous phase, redissolving the continuous phase frozen mixture in a solvent, and introducing the mixture into an effective amount of a nonsolvent to cause the spontaneous formation of microencapsulated product, wherein the solvent and the nonsolvent are miscible and $0<\delta$ solvent $-\delta$ nonsolvent $<6$.

26. The method of claim 25, wherein the solvent, the polymer, and the agent are frozen in liquid nitrogen.

27. The method of claim 25, wherein the microencapsulated product consists of microparticles having an average particle size of between 10 nm and 10 microns.

28. The method of claim 25, wherein the microencapsulated product consists of microparticles having an average particle size between 100 nm and 5 microns.

29. The method of claim 25, wherein the microencapsulated product consists of microparticles having an average particle size of between 100 nm and 1 micron.

30. The method of claim 25, wherein the solvent:nonsolvent volume ratio is >1:40.

31. The method of claim 25, wherein the solvent:nonsolvent volume ratio is >1:50.

* * * * *

UNITED STATES PATENT AND TRADEMARK OFFICE
CERTIFICATE OF CORRECTION

PATENT NO.: 6,143,211
DATED: November 7, 2000
INVENTOR(S): Mathiowitz et al.

It is certified that error appears in the above-identified patent and that said Letters Patent is hereby corrected as shown below:

[73] Brown University Research Foundation,
Providence, R.I.

Signed and Sealed this

Fifteenth Day of May, 2001

*Attest:*

NICHOLAS P. GODICI

*Attesting Officer*   Acting Director of the United States Patent and Trademark Office

UNITED STATES PATENT AND TRADEMARK OFFICE
CERTIFICATE OF CORRECTION

| | | |
|---|---|---|
| PATENT NO. | : 6,143,211 | |
| APPLICATION NO. | : 08/686928 | |
| DATED | : November 7, 2000 | |
| INVENTOR(S) | : Edith Mathiowitz et al. | |

It is certified that error appears in the above-identified patent and that said Letters Patent is hereby corrected as shown below:

Specification, column 1, line 10, insert

--STATEMENT REGARDING FEDERALLY SPONSORED RESEARCH
OR DEVELOPMENT

This invention was made with government support under Grant Number R01 GM55245-06, awarded by the National Institutes of Health. The government has certain rights in the invention.--

Signed and Sealed this
Eighteenth Day of June, 2013

Teresa Stanek Rea
*Acting Director of the United States Patent and Trademark Office*